US010406009B2

(12) United States Patent
Pacetti

(10) Patent No.: US 10,406,009 B2
(45) Date of Patent: Sep. 10, 2019

(54) BIOABSORBABLE SUPERFICIAL FEMORAL STENT PATTERNS WITH DESIGNED TO BREAK LINKS

(75) Inventor: Stephen D. Pacetti, San Jose, CA (US)

(73) Assignee: ABBOTT CARDIOVASCULAR SYSTEMS INC., Santa Clara, CA (US)

(*) Notice: Subject to any disclaimer, the term of this patent is extended or adjusted under 35 U.S.C. 154(b) by 1349 days.

(21) Appl. No.: 12/882,978

(22) Filed: Sep. 15, 2010

(65) Prior Publication Data

US 2012/0065722 A1 Mar. 15, 2012

(51) Int. Cl.
*A61F 2/06* (2013.01)
*A61F 2/915* (2013.01)
*A61F 2/82* (2013.01)

(52) U.S. Cl.
CPC ........ *A61F 2/915* (2013.01); *A61F 2002/826* (2013.01); *A61F 2002/9155* (2013.01); *A61F 2002/91533* (2013.01); *A61F 2210/0004* (2013.01); *A61F 2230/0054* (2013.01); *A61F 2230/0065* (2013.01); *A61F 2250/0036* (2013.01); *A61F 2250/0071* (2013.01)

(58) Field of Classification Search
CPC ....................................................... A61F 2/06
USPC ....................................................... 623/1.16
See application file for complete search history.

(56) References Cited

U.S. PATENT DOCUMENTS

| 5,486,546 | A | 1/1996 | Mathiesen et al. |
| 5,707,385 | A | 1/1998 | Williams |
| 5,919,893 | A | 7/1999 | Roby et al. |
| 5,972,027 | A | 10/1999 | Johnson |
| 6,174,329 | B1 | 1/2001 | Callol et al. |
| 7,169,178 | B1 | 1/2007 | Santos et al. |
| 7,175,873 | B1 | 2/2007 | Roorda et al. |
| 2002/0065553 | A1 | 5/2002 | Weber et al. |
| 2002/0111590 | A1 | 8/2002 | Davila et al. |
| 2003/0083740 | A1 | 5/2003 | Pathak |
| 2003/0181973 | A1 | 9/2003 | Sahota |
| 2004/0034409 | A1 | 2/2004 | Heublein et al. |
| 2004/0093077 | A1 | 5/2004 | White et al. |
| 2004/0147998 | A1 | 7/2004 | Nolting |
| 2004/0167616 | A1 | 8/2004 | Camrud et al. |
| 2004/0215331 | A1 | 10/2004 | Chew et al. |
| 2006/0034888 | A1 | 2/2006 | Pacetti et al. |
| 2006/0173529 | A1* | 8/2006 | Blank .................. 623/1.16 |
| 2006/0195175 | A1* | 8/2006 | Bregulla ............... 623/1.15 |
| 2007/0100431 | A1 | 5/2007 | Bonsignore et al. |
| 2007/0254012 | A1 | 11/2007 | Ludwig et al. |

(Continued)

FOREIGN PATENT DOCUMENTS

DE 10103000 8/2002
EP 1 958 598 8/2008

(Continued)

OTHER PUBLICATIONS

Loo et al., "Radiation effects on poly(lactide-co-glycolide) and poly-l-lactide", Polymer degradation and stability vol. 83, pp. 259-265 (2005).

(Continued)

*Primary Examiner* — Matthew W Schall
(74) *Attorney, Agent, or Firm* — Squire Patton Boggs (US) LLP

(57) ABSTRACT

Bioabsorbable polymeric stent patterns with linking struts between rings that are designed to fail upon deployment of the stent are disclosed.

5 Claims, 17 Drawing Sheets

(56) References Cited

U.S. PATENT DOCUMENTS

| | | |
|---|---|---|
| 2007/0276464 A1 | 11/2007 | Valencia et al. |
| 2007/0288085 A1 | 12/2007 | Furst |
| 2007/0299510 A1 | 12/2007 | Venkatraman et al. |
| 2008/0234195 A1 | 9/2008 | Long et al. |
| 2008/0281393 A1 | 11/2008 | Armstrong et al. |
| 2009/0163989 A1 | 6/2009 | Contiliano et al. |
| 2010/0010622 A1 | 1/2010 | Lowe et al. |

FOREIGN PATENT DOCUMENTS

| | | |
|---|---|---|
| JP | 2007-125394 | 5/2007 |
| WO | WO 2006/138010 | 12/2006 |
| WO | WO 2008/028964 | 3/2008 |
| WO | WO 2008/098776 | 8/2008 |
| WO | WO 2009/137786 | 11/2009 |

OTHER PUBLICATIONS

Yoshioka et al., "Drug release from pol(d-l-lactide) microspheres by gamma irradiation", J. of controller release vol. 37, pp. 263-267 (1995).

International Search Report for PCT/US2011/047574, dated Nov. 7, 2011, 5 pgs.

\* cited by examiner

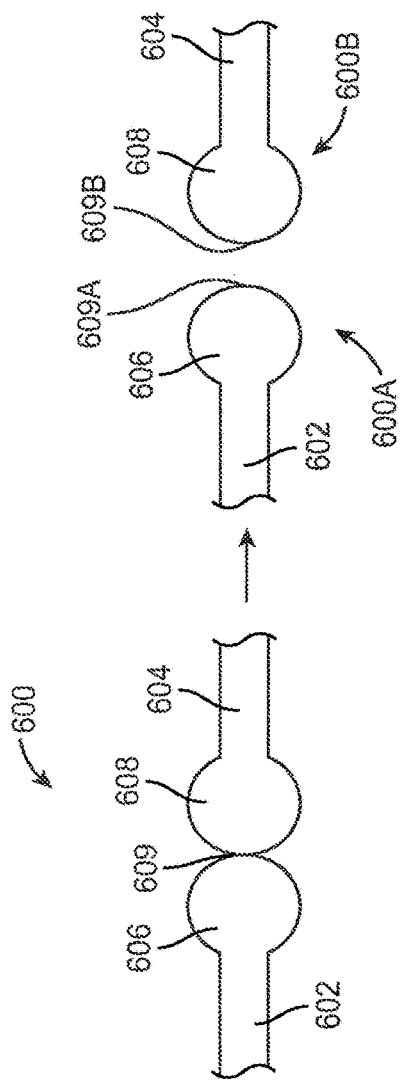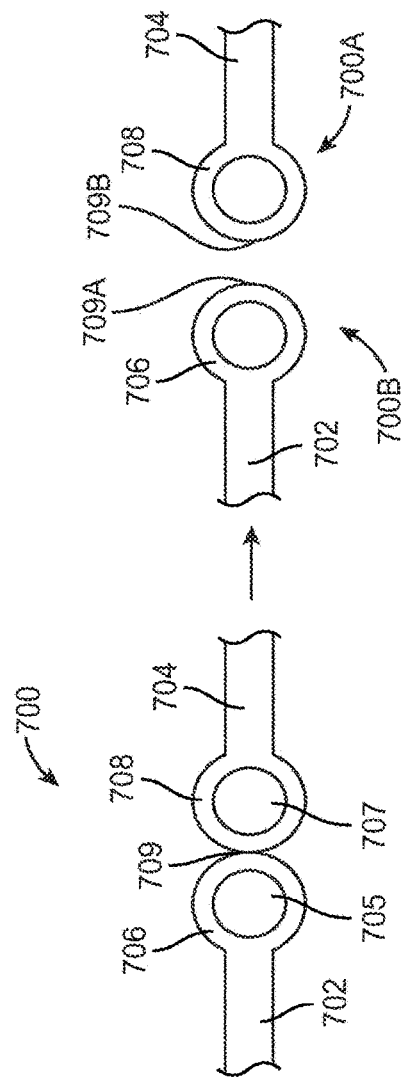

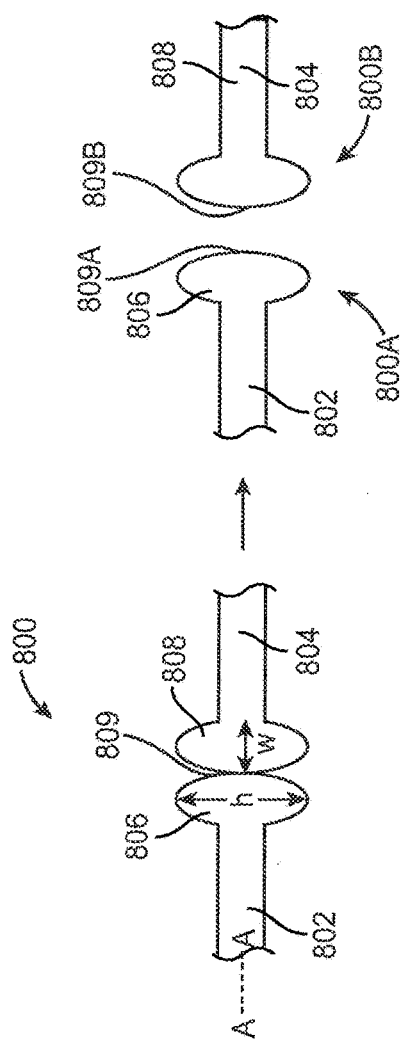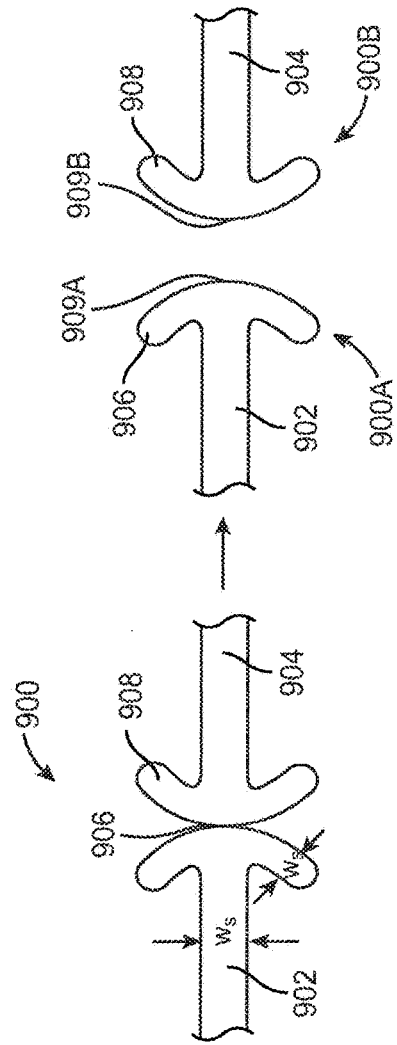

BIOABSORBABLE SUPERFICIAL FEMORAL STENT PATTERNS WITH DESIGNED TO BREAK LINKS

BACKGROUND OF THE INVENTION

Field of the Invention

This invention relates to methods of treatment of blood vessels with bioabsorbable polymeric medical devices, in particular, stents.

Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of acute closure and restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. The therapeutic substance can also mitigate an adverse biological response to the presence of the stent. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of either a metallic or polymeric scaffolding with a polymeric carrier that includes an active or bioactive agent or drug. Polymeric scaffolding may also serve as a carrier of an active agent or drug by incorporating a drug through the scaffolding material.

The stent must be able to satisfy a number of mechanical requirements. The stent must be have sufficient radial strength so that it is capable of withstanding the structural loads, namely radial compressive forces, imposed on the stent as it supports the walls of a vessel. This structural load will change as a function of time as the vessel heals, undergoes positive remodeling, or adapts to the presence of the stent.

Once expanded, the stent must adequately provide lumen support during a time required for treatment in spite of the various forces that may come to bear on it, including the cyclic loading induced by the beating heart. In addition, the stent must possess sufficient flexibility with a certain resistance to fracture.

Stents made from biostable or non-erodible materials, such as metals, have become the standard of care for percutaneous coronary intervention (PCI) as well as in peripheral applications, such as the superficial femoral artery (SFA), since such stents have been shown to be capable of preventing early and late recoil and restenosis. For a variety of reasons, the performance of stents in the SFA appear to be more problematic than in coronary vessels and in other peripheral vascular beds, such as the iliac and carotid arteries.

This may be due to the significant mechanical stresses placed on the devices in the dynamic SFA environment relative to other vasculature, as well as the vessel length and the severity of stenotic and occlusive disease. The SFA is subjected to various forces, such as compression, torsion, flexion, extension, and contraction, which place a high demand on the mechanical performance of implants.

SUMMARY OF THE INVENTION

Various embodiments of the present invention include a stent for treating a diseased section of a blood vessel, comprising: a bioabsorbable polymeric scaffolding composed of a pattern of struts, the pattern comprising a first cylindrical ring of struts and a second cylindrical ring of struts, wherein the first ring and the second ring are connected by a set of breakable linking struts having a smaller radial thickness than struts of the cylindrical rings, and wherein the thin linking struts break after deployment of the stent in a vessel of a patient prior to struts in the cylindrical rings.

Further embodiments of the present invention include a stent for treating a diseased section of a blood vessel, comprising: a bioabsorbable polymeric scaffolding composed of a pattern of struts, the pattern comprising a first cylindrical ring of struts and a second cylindrical ring of struts, wherein the first ring and the second ring are connected by a set of breakable linking struts, wherein two or more adjacent holes are disposed in an abluminal surface of each linking strut midway between the first and second cylindrical rings, and wherein after deployment of the stent in a vessel of a patient each link breaks at the position of the holes prior to struts in the cylindrical rings.

Additional embodiments of the present invention include a stent for treating a diseased section of a blood vessel, comprising: a bioabsorbable polymeric scaffolding composed of a pattern of struts, the pattern comprising a first cylindrical ring of struts and a second cylindrical ring of struts, wherein the first ring and the second ring are connected by a set of breakable linking struts, wherein a slot is disposed in an abluminal surface of each linking strut midway between the first and second cylindrical rings, and wherein after deployment of the stent in a vessel of a patient each link breaks at the position of the slot prior to struts in the cylindrical rings.

Other embodiments of the present invention include a stent for treating a diseased section of a blood vessel, comprising: a bioabsorbable polymeric scaffolding composed of a pattern of struts, the pattern comprising a first cylindrical ring of struts and a second cylindrical ring of struts, wherein the first ring and the second ring are connected by a set of breakable linking struts, wherein each breakable linking strut has two disc-like features disposed between the rings, wherein the disc-like features are connected at their curved surfaces which forms a notch at the connection point, wherein after deployment of the stent in a vessel of a patient each link breaks at the connection point prior to struts in the cylindrical rings.

Additional embodiments of the present invention include a stent for treating a diseased section of a blood vessel, comprising: a bioabsorbable polymeric scaffolding composed of a pattern of struts, the pattern comprising a first cylindrical ring of struts and a second cylindrical ring of struts, wherein the first ring and the second ring are connected by a set of breakable linking struts, wherein each breakable linking strut comprises two opposing anchor-shaped elements, wherein each anchor-shaped element is composed of a straight segment and a curved segment disposed between the rings, wherein the curved segments of the breakable linking struts are connected at their convex curved surfaces to form a notch at the connection point, wherein after deployment of the stent in a vessel of a patient each link breaks at the connection point prior to struts in the cylindrical rings.

BRIEF DESCRIPTION OF THE DRAWINGS

FIG. 14A depicts a link including two discs disposed between cylindrical rings, the two discs connected at their curved surfaces and forming a notch.

FIG. 14B depicts the link of FIG. 14A after failure of the link at the notch.

FIG. 15A depicts a link including two discs with holes disposed between cylindrical rings, the discs connected at their curved surfaces and forming a notch.

FIG. 15B depicts the link of FIG. 15A after failure of the link at the notch.

FIG. 16A depicts a link including two oblate discs disposed between cylindrical rings, the oblate discs connected at their curved surfaces and forming a notch.

FIG. 16B depicts the link of FIG. 16A after failure of the link at the notch.

FIG. 17A depicts a link including two curved struts disposed between cylindrical rings, the curved struts connected at their curved surfaces and forming a notch.

FIG. 17B depicts the link of FIG. 17A after failure of the link at the notch.

DETAILED DESCRIPTION OF THE INVENTION

Figure 1:
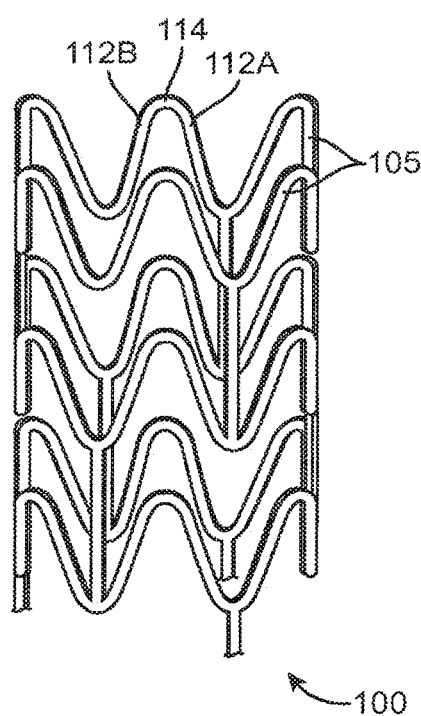
FIG. 1 depicts an exemplary stent.

Coronary arteries refer generally to arteries that branch off the aorta to supply the heart muscle with oxygenated blood. Peripheral arteries refer generally to blood vessels outside the heart and brain.

In both coronary artery disease and peripheral artery disease, the arteries become hardened and narrowed or stenotic and restrict blood flow. In the case of the coronary arteries, blood flow is restricted to the heart, while in the peripheral arteries blood flow is restricted leading to the kidneys, stomach, arms, legs and feet. The narrowing is caused by the buildup of cholesterol and other material, called plaque, on their inner walls of the vessel. Such narrowed or stenotic portions are often referred to as lesions. Arterial disease also includes the reoccurrence of stenosis or restenosis that occurs after an angioplasty treatment. Although there are probably several mechanisms that lead to restenosis of arteries, an important one is the inflammatory response, which induces tissue proliferation around an angioplasty site. The inflammatory response can be caused by the balloon expansion used to open the vessel, or if a stent is placed, by the foreign material of the stent itself.

In the area of peripheral therapies, treatment of lesions of the superficial femoral artery remains problematic. The current best therapy is Percutaneous Transluminal Angioplasty (PTA) followed by implantation of a self-expanding stent. However, restenosis rates, particularly for longer lesions, remain high. For example, in one trial using Dynalink or Absolute stents, with an average lesion length of 133 mm, the restenosis rate at one year was 37%. Drug eluting stents consisting of drug eluting coating on a nitinol stent have been tried. The best examples are the SCIROCCO and STRIDES trials. In both of these trials, the patency rates at one year were no better than with a bare nitinol stent. Not surprisingly, a drug eluting, totally bioabsorbable stent has been proposed as a solution. In the SFA, good patency rates at 6 months are not enough as in the overwhelming majority of trials, restenosis and late loss continue to increase at the 12 month time point. This raises the question of how a bioabsorbable SFA stent can be designed which will have a higher patency rate that a drug eluting nitinol stent at the critical 12 month time point.

It has been proposed that a bioabsorbable drug eluting scaffold which has the same patency rate at 12 months as a bare nitinol stent, or a drug eluting nitinol stent, would be a worthwhile product. This is because even if the bioabsorbable scaffold restenoses at 12 months, the bioabsorbable scaffold can be re-intervened upon.

A totally bioabsorbable SFA stent scaffold, for example a poly(L-lactide) scaffold, undergoes a high degree of flex, elongation and torsion after implantation. The amount of movement is greater than what a coronary scaffold experiences in the coronary artery. A polymeric SFA scaffold may experience significant strut cracking after a few weeks implantation. Strut breakage is not inherently deleterious so long as the following issues are under control: scaffold needs to maintain radial strength for the needed length of time. The radial strength is primarily attributable to the integrity of the rings in the stent and not the links; strut breakage is not so numerous that fragments are released; strut breakage does not release high levels of particulate; and broken struts must not be mechanically injurious to the vessel leading to tissue irritation or even vessel dissection and perforation.

Embodiments of the present invention are applicable to endovascular treatment of coronary and peripheral disease in coronary arteries and various peripheral vessels including the superficial femoral artery, the iliac artery, and carotid artery. The embodiments are further applicable to various stent types, such as self-expandable and balloon expandable stents. The embodiments are further applicable to various stent designs including scaffolding structures formed from tubes, wire structures, and woven mesh structures.

In embodiments of the present invention, a stent includes a plurality of cylindrical rings connected or coupled with linking elements. When deployed in a section of a vessel, the cylindrical rings are load bearing and support the vessel wall at an expanded diameter or a diameter range due to cyclical forces in the vessel. Load bearing refers to the supporting of the load imposed by radial inwardly directed forces. Structural elements, such as the linking elements or struts, are non-load bearing, serving to maintain connectivity between the rings. For example, a stent may include a scaffolding composed of a pattern or network of interconnecting structural elements or struts.

FIG. 1 depicts a view of an exemplary stent 100. In some embodiments, a stent may include a body, backbone, or scaffolding having a pattern or network of interconnecting structural elements 105. Stent 100 may be formed from a tube (not shown). FIG. 1 illustrates features that are typical to many stent patterns including cylindrical rings 107 connected by linking elements 110. (FIG. 1 is missing 107 and 110) As mentioned above, the cylindrical rings are load bearing in that they provide radially directed force to support the walls of a vessel. The linking elements generally function to hold the cylindrical rings together. The stent 100 includes bending elements composed of, for example, struts 112A and 112B that are joined at an apex or a crown 114. When stent 100 is expanded to a deployed or deployment diameter, struts 112A and 112B bend resulting in plastic deformation at apex 114.

The structural pattern in FIG. 1 is merely exemplary and serves to illustrate the basic structure and features of a stent pattern. A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed on a tube or sheet with a technique such as laser cutting or chemical etching. The stent can then be crimped on to a balloon or catheter for delivery into a bodily lumen.

In embodiments of the present invention, the bioabsorbable stent is deployed at a diseased section of a vessel. The deployed stent expands the diseased section to a deployment diameter to form a stented segment. The initial clinical need for any stent is to provide mechanical support to maintain patency or keep a vessel open at or near the deployment diameter. The stent is designed to have sufficient radial strength to maintain such patency for a period of time.

The patency provided by the stent allows the stented segment of the vessel to undergo healing and remodeling at the increased diameter. Remodeling refers generally to structural changes in the vessel wall that enhance its load-bearing ability. The high radial strength of the stent tends to freeze the size of the vessel a period of time to enable remodeling at the increased size. During this time period, the stent inhibits or prevents the natural pulsatile function of the vessel. In general, with balloon expandable stents some pulsatile motion still exists, while with self-expanding stents the vessel can undergo even more pulsatile motion.

The stent structure prevents recoil and maintains a circular lumen while the vessel remodels and molds itself to the stented diameter, which corresponds to positive remodeling. Early recoil before sufficient modeling takes place can result in negative remodeling, referring to molding of the stent to a diameter significantly less than the original stented diameter.

A period of patency is required in order to obtain permanent positive remodeling and vessel healing. However, the vessel requires the patency for only a finite time to obtain such positive remodeling. As the polymer of the stent degrades, the radial strength of the stent decreases and the load of the vessel is gradually transferred from the stent to the remodeled vessel wall. Remodeling of the vessel wall can continue even after loss of radial strength of the stent.

The drop in radial strength is not necessarily due to fracture or breaking of the stent scaffolding. For example, for a stent scaffolding, such as that in FIG. 1, the radial strength loss is preferably due to degradation of strength of the polymer in the bending regions. The molecular weight of the polymer in these regions degrades and eventually the polymer is unable to oppose the inwardly directed force imposed by the vessel wall. The decrease in the molecular weight of the polymer leads to a loss in strength. The stent scaffolding then exhibits a controlled loss in radial strength. Controlled loss of radial strength refers to the loss without dislodgement of particulate material that can cause thromboembolitic events. Decline in radial strength due to fracture or breaking of the stent scaffolding can lead to such dislodgement.

In addition to the decline in radial strength, the degradation of the stent also causes a gradual decline in the mechanical integrity. Mechanical integrity refers to the connectivity of struts and the size and shape of the overall stent structure. The stent may be designed to lose mechanical integrity in a controlled manner that avoids dislodgement of stent material which can cause thrombo-embolitic events. In some embodiments, non-load bearing members are designed to fracture and break before load-bearing members. In such embodiments, non-load bearing members are selectively modified to induce such failure.

Additionally, the bioabsorbable stent can include a polymeric drug release coating. The coating can include a bioabsorbable polymer mixed with an antiproliferative drug for the control of smooth muscle cell proliferation (SMP). SMP is a biological response of the vessel and is part of the remodeling process. However, if it is not controlled, SMP can cause restenosis. The stent of the present invention is designed to provide a drug release profile which controls smooth muscle cell proliferation during the initial phase when stimulation to proliferate is greatest, but terminates soon enough to allow complete or almost complete endothelialization of stent struts prior to substantial mass loss and mechanical integrity loss. "Almost complete" can correspond to at least 90% of struts covered by an endothelial layer. Specifically, the stent may be designed to have a drug release profile that declines to zero between 3-4 months after intervention.

Endothelialization is an important part of the healing process with a bioabsorbable stent. Both the degree of endothelialization and timing of the endothelialization with respect to the other stent behavior are important features. Endothelialization refers to coverage of a surface with endothelial tissue or endothelial cells. Complete or almost complete endothelialization of the vessel wall and stent struts is essential to prevent thrombosis associated with blood contacting stent surfaces. Incorporation of the stent into the vessel wall by a controlled amount of neointimal formation will prevent incomplete strut apposition (persistent or late-acquired), and dislodgement of particulate stent material. Additionally, the timing of the endothelialization with respect to mechanical integrity loss and mass loss is also an important aspect of the healing process.

The presence of a blood-contacting surface of a foreign body regardless of the level of hemo-compatibility presents a risk of thrombosis. In general, endothelialization plays a crucial role in reducing or preventing vascular thrombosis and intimal thickening. Specifically, the endothelial coverage reduces or prevents deposition of proteins, fibrin and thrombus on the vessel wall or stent struts. Such deposition can contribute to or increase risk of thrombosis. Therefore, early and complete endothelialization of the vessel wall and stent are essential. The stent is designed to allow for complete or almost complete endothelialization of stent struts between 4 and 6 months after deployment. Such a range can be achieved through the use of small enough strut dimensions (e.g., a cross-section of 150×150 microns), a biocompatible scaffolding material such as a biodegradable polyester, and a drug release profile that provides complete release by about 4 months.

In various embodiments of present invention, particular structural elements or types of structural elements can be designed to fail before others. In certain embodiments, linking elements between rings of a stent structure can fail resulting in partial or complete loss of connectivity between adjacent cylindrical rings. The cylindrical rings can remain intact for a period of time and maintain a circular shape. The cylindrical rings are decoupled which allows for greater flexing or pulsatile motion of the stented vessel. A decoupled ring refers to a ring that is not connected to another ring by linking elements.

In some embodiments, the initial loss in mechanical integrity occurs at linking elements. In one embodiment, the linking elements between rings of a stent structure can fail which results in partial or complete loss of connectivity between adjacent cylindrical rings. The decoupled rings retain sufficient radial strength to support the vessel at or near the deployed diameter.

In certain embodiments, the rings are not covered or are only partially covered by endothelial tissue when mechanical integrity starts to fail. The rings can be covered by endothelial tissue after mechanical integrity starts to fail or, specifically, after the rings become decoupled due to failure of the linking elements. In other embodiments, the rings may be completely covered or incorporated by an endothelial layer before mechanical integrity starts to fail.

Figure 2A:
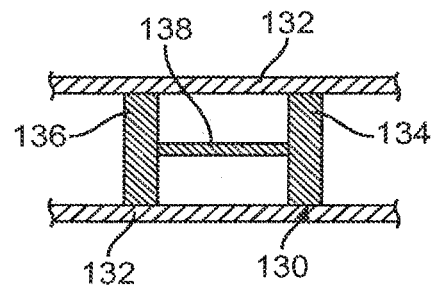
FIGS. 2A-C illustrate the failure of linking elements of a stent pattern.
Figure 2B:
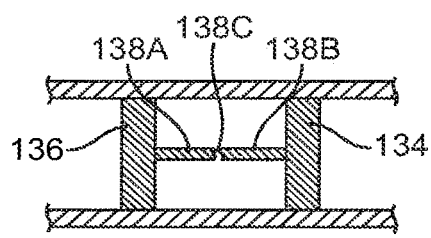
Figure 2C:
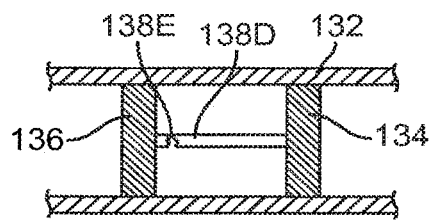

FIGS. 2A-C illustrate the failure of linking elements of a stent pattern. FIGS. 2A-C depict a two-dimensional projection of a stent 130 deployed in a segment of a vessel with walls 132. Stent 130 has rings 134 and 136 that are opposed against wall 132. The structure of rings 134 and 136 is not shown. Rings 134 are connected by linking elements which are exemplified by linking element 138.

FIG. 2B depicts failure of linking element 138 which has broken apart at point 138C into segments 138A and 138B. FIG. 2C depicts failure of linking element 138 broken into segments 138D at point 138E, the intersection of ring 136 and linking element 138.

In some embodiments, some or all of the rings can be decoupled from one another. In one embodiment, all of the rings are decoupled. In another embodiment, pairs or triples of rings remain coupled and are decoupled from adjacent single rings, ring pairs, or ring triples.

Figure 3A:
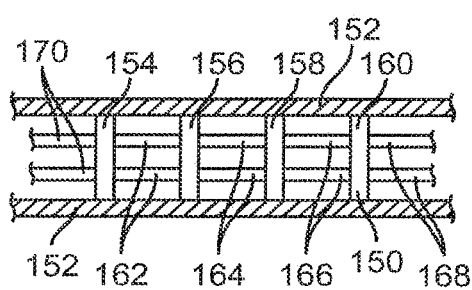
FIG. 3A depicts a two-dimensional projection of a stent with rings connected by linking elements deployed in a segment of a vessel.
Figure 3B:
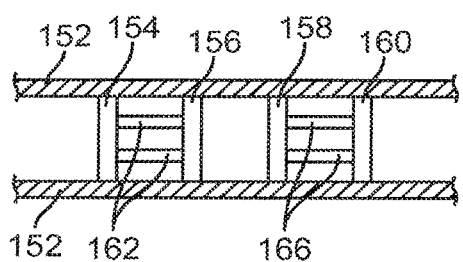
FIG. 3B depicts the stent of FIG. 3A with two disconnected ring pairs that are disconnected due to failure of linking elements between the pairs.

FIG. 3A depicts a two-dimensional projection of a stent 150 deployed in a segment of a vessel with a wall 152. Stent 150 has rings 154, 156, 158, and 160 that are opposed against a vessel wall 152. The rings have linking elements 162, 164, 166, 168 and 170. Linking elements 164, 168, and 170 are designed to fail leaving pairs of rings 154-156 and 158-160 connected. FIG. 3B depicts stent 150 with ring pair 154-156 connected and ring pair 158-160 connected. Ring pairs 154-156 and 158-160 are disconnected due to failure of linking elements 164, 168, and 170 (not shown).

These embodiments are useful for maintaining patency in vessels such as the SFA which are subject to significant forces due to compression, torsion, flexion, extension, and contraction. In general, it is particularly useful in vessels that impart stresses on the stent structure that are not radially directed, for example, forces that place stress on the stent along a longitudinal, flexural, or helical direction. Longitudinal stresses can arise from longitudinal compression and extension, flexural stresses are imposed by lateral flexing, while helical stress can arise from torsional forces. Such stresses are propagated along the length of the stent and can impart significant stress and strain throughout the stent structure. In particular, forces due to compression, torsion, flexing, and extension can be transmitted by linking struts connecting rings to the rings, causing failure to the rings. The stresses and strain can be imparted in sections of the structure and along axes that are not designed to be load bearing. Decoupling the rings or sections of rings from one another reduces or eliminates such stress and failure of rings.

Additionally, the embodiments of decoupled rings are advantageous in vessel segments that have a significant degree of curvature. The decoupling of rings reduces or prevents propagation of failure to rings due to bending of the stent structure along its axis. The decoupling also allows individual rings or decoupled sections rings the freedom to orient in a manner that maximizes the support of the lumen, i.e., the opening of a ring coincides more closely with the lumen opening.

The decoupling of the rings is particularly advantageous for treating curved sections of vessels, both coronary and peripheral. Curvature in vessels may arise or be increased from increased physiological demands caused by physical exertion or movement. In this case, the curvature changes with time depending on the level of physical exertion. Additionally, there are sections of vessels that have curvature even in the absence of increased physiological demands. Since the rings are decoupled, the rings fit around or follow the natural curvature of the vessel. The decoupled rings cause minimal or no stress tending to decrease the curvature away from a natural state. The decoupled rings also cause minimal or no stress that tends to inhibit changes in curvature due to physiological demands. When the curvature of the vessel changes with time due to physiological demands, the decoupled rings allow the vessel curvature to change. This is in contrast to a metallic stent that tends to decrease the natural curvature or inhibit changes in curvature which causes additional stress to the section.

The preference for decoupled single rings or sections of rings depends on the degree of non-radially directed forces and the degree of bending of the vessel. The greater the forces, degree of bending, or both, then decoupled single rings or a smaller sections (e.g., pairs of rings) is preferred.

While decoupled rings can be very advantageous at some time after stent deployment, they are not preferred for the stent in its initially manufactured state. With no links it is very challenging to maintain the ring elements in their proper orientations with respect to one another. This is the case during stent manufacturing, assembling the stent onto the delivery system, and during delivery of the stent to the target lesion.

Further embodiments of the present invention include a bioabsorbable stent designed to have selective failure of structural elements to provide the controlled loss of mechanical strength described above. In such embodiments, selected structural elements can be designed to fail or break before other structural elements that remain free of fractures or unbroken for a period time. These selected structural elements can be designed to fail at about the same time.

The selected structural elements can be non-load bearing elements, such as linking struts. Some or all of the non-load bearing or linking struts can be designed to fail or break, for example in the manner described above. When the selected structural elements break, the unbroken structural elements, can continue to serve a clinical need, such as rings that provide support to a vessel wall. Additionally or alternatively, the unbroken elements can remain intact until covered by endothelial tissue.

The selected structural elements can have a property or feature that makes the structural elements susceptible to failure sooner than structural elements that are free of the property or feature upon deployment of the stent in a living body. The selected structural elements or regions thereof can be selectively designed or modified to have the property or feature that is different than unmodified regions.

Figure 4:
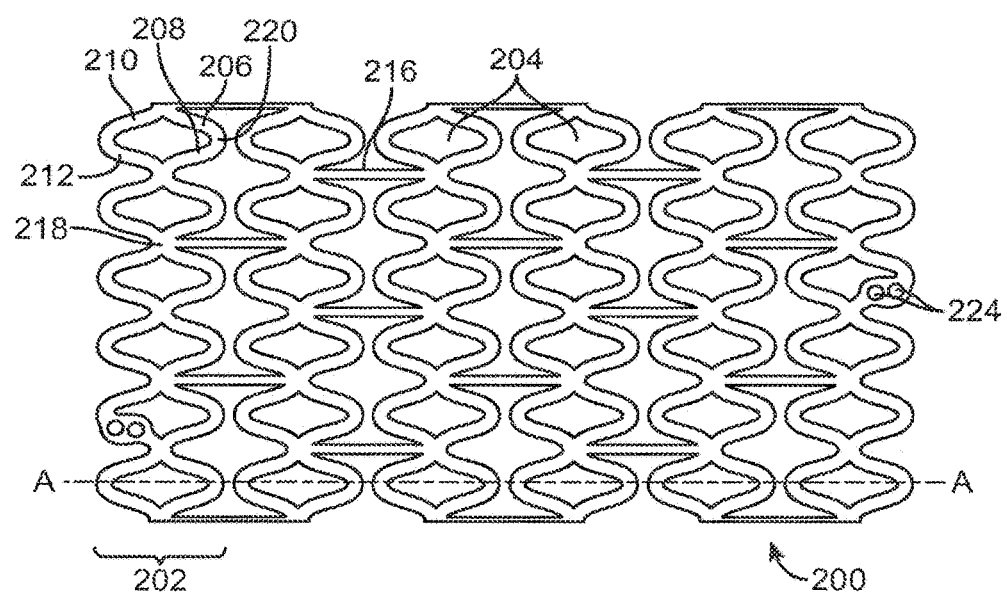
FIG. 4 depicts an exemplary stent pattern for illustrating selective failure of stent struts.

FIG. 4 depicts an exemplary stent pattern 200 for illustrating selective failure of stent struts. Stent pattern 200 is shown in a flattened condition so the pattern can be clearly viewed. When the flattened portion of stent pattern 200 is in a cylindrical form, it forms a radially expandable stent. Stent pattern 200 includes a plurality of cylindrical rings 202 with each ring made up of a plurality of diamond shaped cells 204. Linking struts 216 connect adjacent cylindrical rings. Linking struts 216 are parallel to line A-A and connect adjacent rings between intersection 218 of cylindrically adjacent diamond-shaped elements 204 of one ring and intersection 218 of cylindrically adjacent diamond shaped elements 204 of an adjacent ring.

Stent pattern 200 can have any number of rings 202 depending on a desired length of a stent. For reference, line A-A represents the longitudinal axis of a stent using the pattern depicted in FIG. 4. Diamond shaped cells 204 are made up of struts 206 and 208 that form a curved element and struts 210 and 212 that form an opposing curved element. Pattern 200 includes pairs of holes 224 in struts at both ends of the stent to accommodate radiopaque markers.

Figure 5:
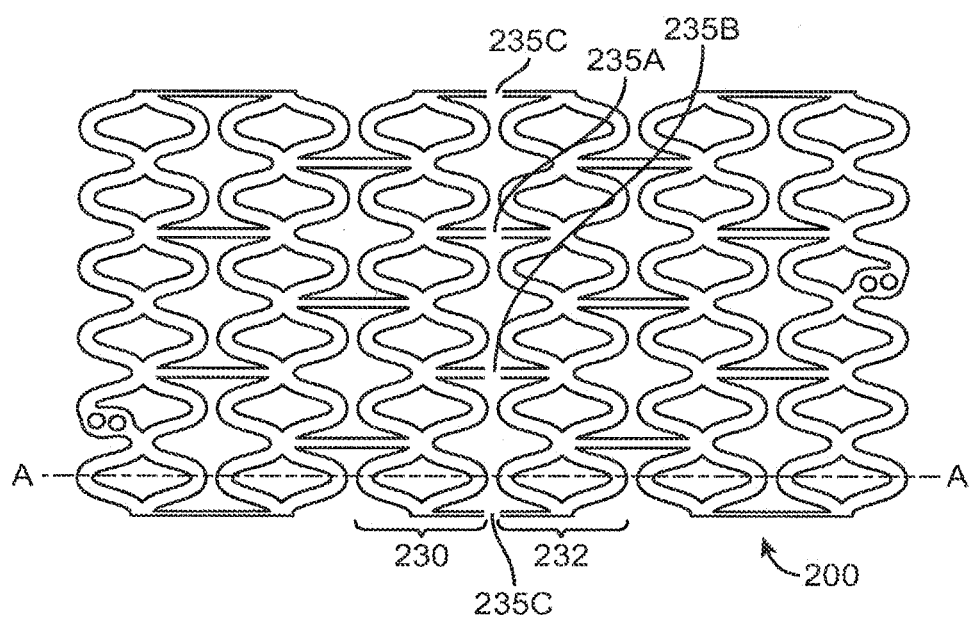
FIGS. 5-7 depict the pattern of FIG. 4 with decoupled rings.

In certain embodiments, the selective failure of structural elements disconnects or decouples at least one pair of adjacent rings. In one embodiment, each of the linking struts that connects a pair of adjacent rings is selectively modified to fail. In FIG. 5, which depicts the pattern of FIG. 4, a pair of adjacent rings, 230 and 232, are decoupled by the selective failure of linking struts 235A, 235B, and 235C. Such a failure results in decoupling the stent into two sets of rings of equal number.

In all embodiments, 10-50%, 50-90%, or 90-99% of the connecting links may be intact (not decoupled) immediately after deployment in a human patient. In all embodiments, at least 10%, 50%, 90%, or 99% of the connecting links may be intact immediately after deployment in a human patient.

Figure 6:
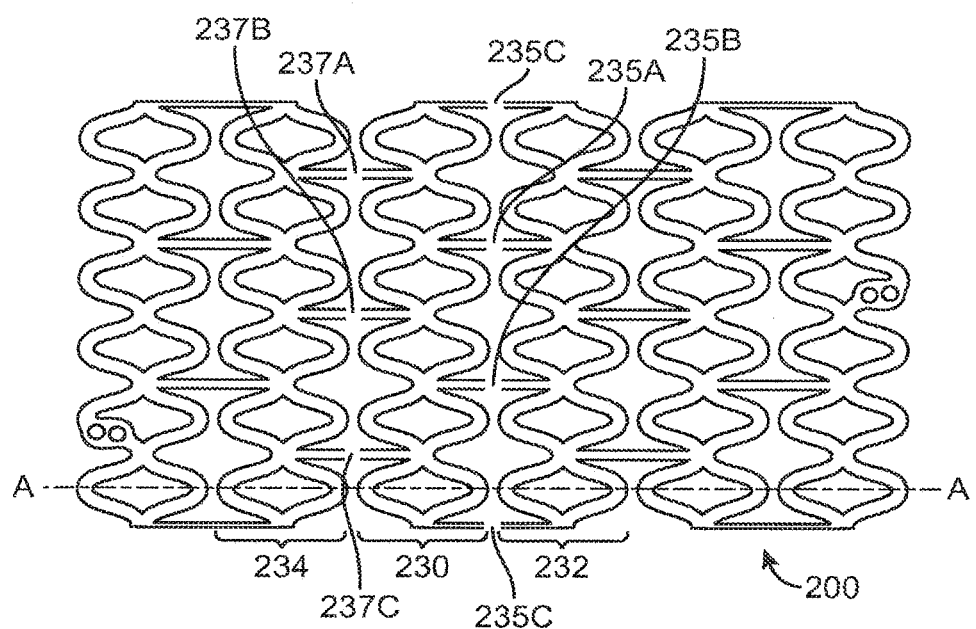

The selective failure can also include decoupling at least one ring or group of consecutive rings completely from adjacent rings. The selected structural elements include all of the linking struts that connect the ring or the consecutive group of rings to adjacent rings. In FIG. 6, ring 230 is decoupled from rings 232 and 234 by the selective failure of linking struts 235A-C and linking struts 237A-C, respectively.

Figure 7:
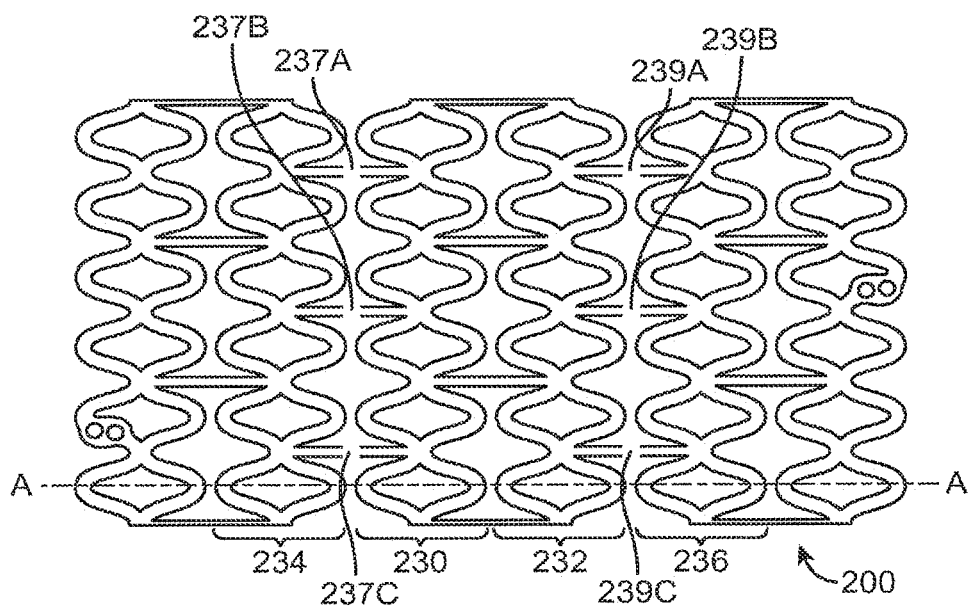

Similarly, referring to FIG. 7, consecutive ring pair 230-232 is decoupled from rings 234 and 236 by failure of linking struts 237A-C and linking struts 239A-C, respectively. In FIG. 6, the stent is broken up into three sets of rings of unequal number, two, one, and three. In FIG. 7, the stent is broken up into three sets of rings of equal number.

The selected failure can also include decoupling all of the rings or all groups of consecutive rings completely. With the pattern of FIG. 5, failure of all of the linking struts would result in six decoupled rings.

The manner of failure that is desirable depends upon the type and degree of force to which a deployed stent is subjected. As the degree of flexing, torsion and longitudinal compression and extension increases, smaller and more sets of decoupled rings are desirable.

Figure 8:
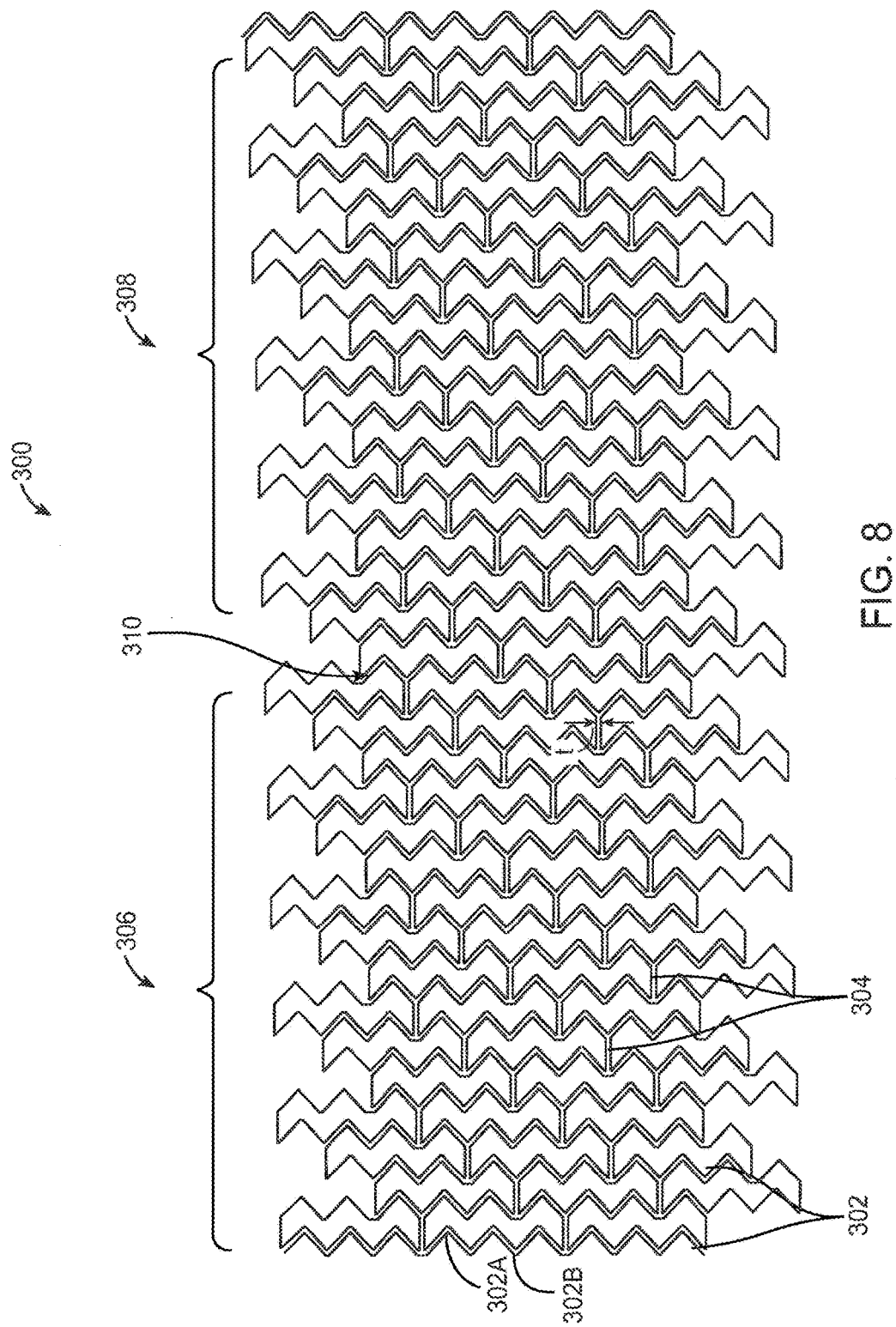
FIG. 8 depicts another exemplary stent pattern for illustrating selective failure of stent struts.

FIG. 8 depicts another exemplary stent pattern 300 for illustrating selective failure of stent struts. Stent pattern 300 is also shown in a flattened condition. Stent pattern 300 includes a plurality of cylindrical rings 302 with each ring made up of a plurality of undulating struts with peaks 302A and valleys 302B. Linking struts 304 connect adjacent cylindrical rings by connecting the valley of one ring to the valley of the adjacent ring.

Figure 9A:
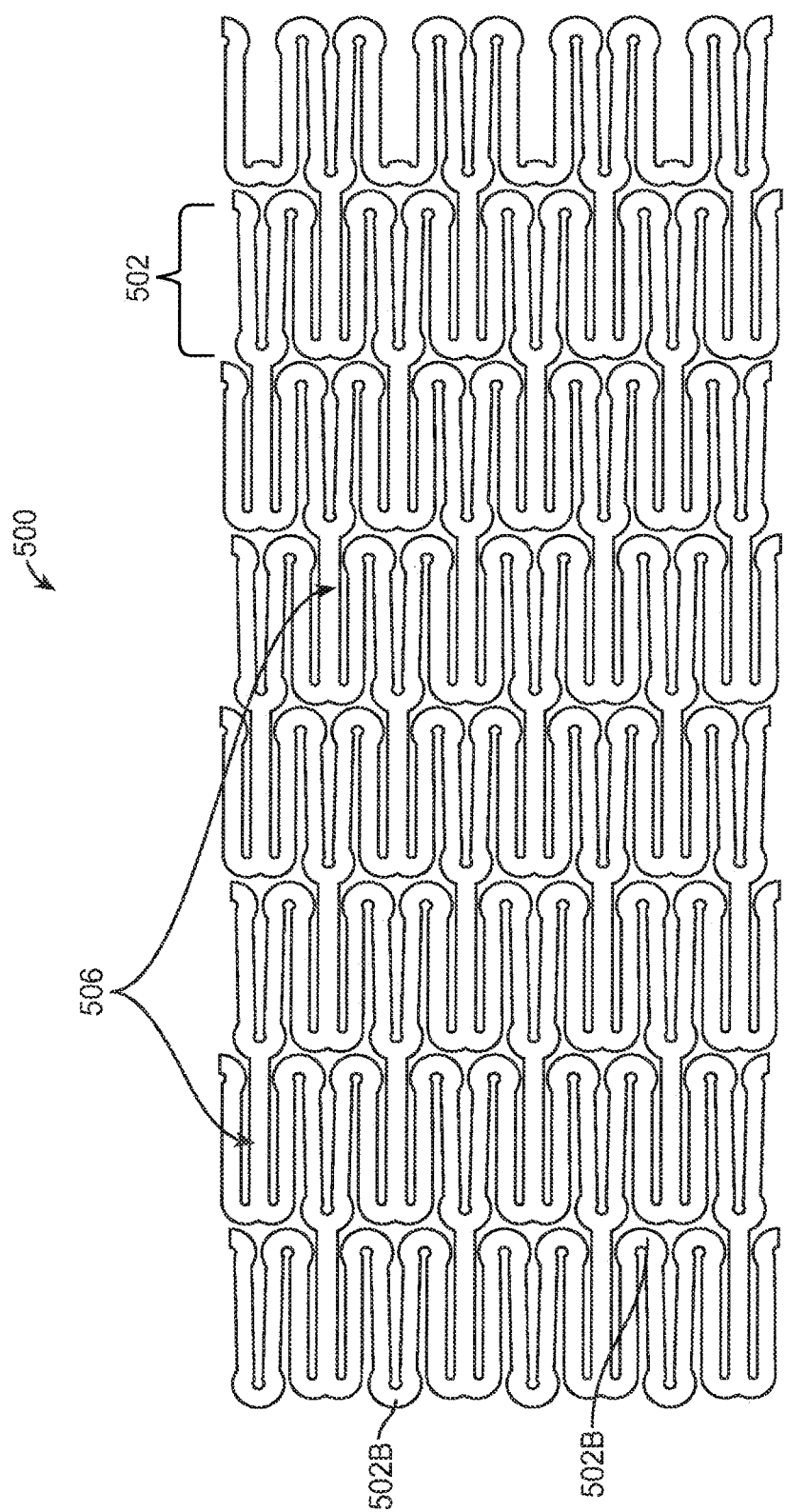
FIG. 9A depicts a portion of another exemplary stent pattern in a crimped or compressed state.
Figure 9B:
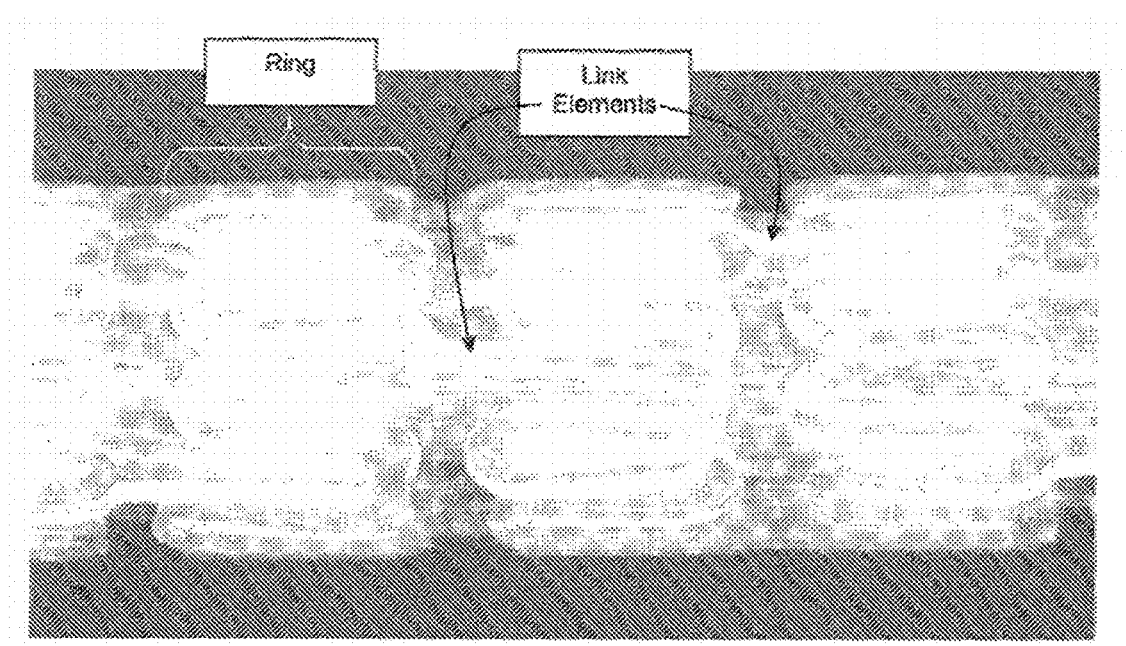
FIG. 9B depicts a photograph of the pattern in FIG. 9A.

FIG. 9A depicts a portion of another exemplary stent pattern 500 in a crimped or compressed state. Stent pattern 500 includes a plurality of cylindrical rings 502 with each ring made up of a plurality of undulating struts with peaks 502A and valleys 502B. Linking struts 506 connect adjacent cylindrical rings by connecting the valley of one ring to the valley of the adjacent ring. FIG. 9B depicts a photograph of such an exemplary stent pattern crimped onto a balloon catheter. In certain embodiments, a period of time after implantation in a vessel, a proximal axial portion of a stent, for example, proximal axial portion 306 in FIG. 8, is designed to decouple or separate from a distal axial portion 308 through selective fracture of linking struts at ring 310. In an exemplary embodiment, the stent can be designed for treatment of the SFA with an exemplary length of about 10 cm or about 15 cm. In one embodiment, weeks or months after implantation, the 10 cm stent separates into two 5 cm sections. In another embodiment, the 15 cm stent can separate into three 5 cm sections.

The linking struts that are designed or preprogrammed to selectively fail prematurely, for example, at ring 310, can have a structure that results in the linking struts selectively failing or fracturing, causing separation of axial sections of the stent.

For a laser cut polymeric scaffold, the strut thickness is largely determined by the wall thickness of the polymeric hypotubing. As it is easiest to make the hypotubing of constant wall thickness, it is easiest to make the links and bar arms in the rings all the same thickness. Consequently, one way to make the link easier to break, and thus to selectively fail, is to make it narrower. Therefore, in one embodiment, some or all of the linking struts at a selected axial location or ring have a side wall to side wall thickness, ts, less than struts in the cylindrical rings or linking struts that are not designed to selectively fail prematurely, for example, linking struts in portions 306 and 308. For instance, the linking struts can have a side wall to side wall thickness that is 0.1 to two thirds the width of cylindrical ring struts or linking struts that are not designed to fail prematurely. In some embodiments, all linking struts around a ring can be designed to selectively fail at selected axial locations, for example, every 6 cm±3 cm.

Figure 10A:
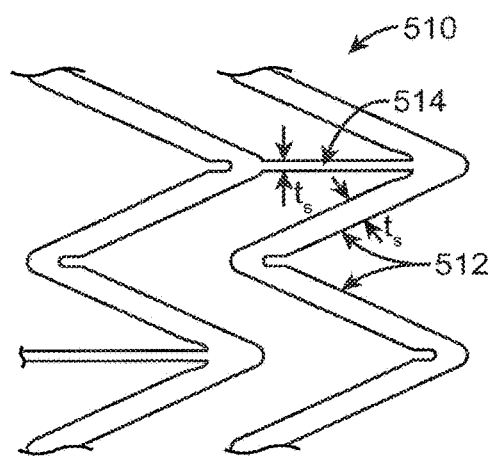
FIG. 10A depicts a portion of a stent pattern showing wider or thicker ring elements and narrower or thinner links.

Another example is shown in FIG. 10A which depicts a portion 510 of a stent pattern showing wider or thicker cylindrical ring struts 512 and narrower or thinner link struts 514 with a ts less than the ts of ring struts 512.

In other embodiments, some or all of the linking struts at a selected axial location or ring have a radial thickness, tr, less than struts in cylindrical rings or linking struts that are not designed to selectively fail prematurely. The radial thickness is the thickness of a strut from the luminal surface to the abluminal surface. For example, the linking struts can have a radial thickness that is 0.1 to two thirds the thickness of struts of cylindrical rings or linking struts that are not designed to fail prematurely. In some embodiments, all linking struts around a ring can be designed to selectively fail at selected axial locations, for example, every 6 cm±3 cm.

Figure 10B:
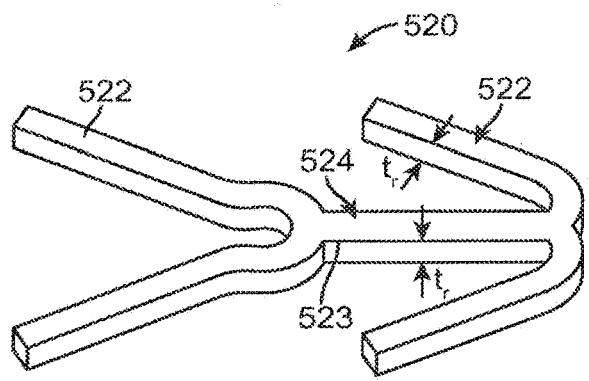
FIG. 10B depicts a portion of a stent pattern showing wider or thicker ring elements and narrower or thinner links with a radial thickness less than the radial thickness of ring elements.

FIG. 10B depicts a portion 520 of a stent pattern showing a wider or thicker ring struts 522 and narrower or thinner links 524 with a radial thickness less than the radial thickness of ring struts 522. As shown, there can be a transition region or tapering 523 from the radial thickness of the ring struts 522 to the thickness of the link struts 523. The tapering can occur over a short distance, as shown in FIG. 10B, with the remainder of the linking strut being a uniform thickness. Alternatively, the tapering can be gradual, occurring along most or all of the length of the linking struts. In one embodiment, the radial thickness can decrease gradually from the connection points of the linking struts to the ring struts to the midpoint of the linking struts.

A scaffold where the links have a smaller radial thickness than the struts in the rings may be made from a variable wall thickness hypotubing. Variable thickness polymeric hypotubing could be made by machining the wall thinner. Another method would be to vary the draw speed of the tubing out of the extruder to produce variable thickness hypotubing. Proper registration can be maintained of the thinner tube regions with the stent pattern when the stent is cut.

Figure 11:
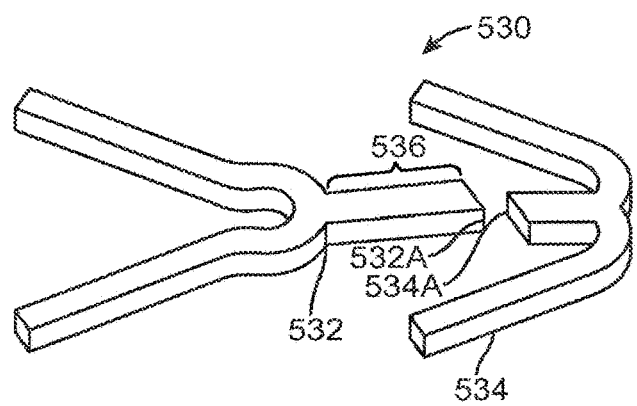
FIG. 11 which shows a portion of a stent pattern that is fractured into a two pieces.

A potential disadvantage with thinner struts is that the location of the fracture of the link is not predictable. The fracture is somewhat uncontrolled and would likely occur near or at a strut junction. This may not be desirable as it could result in a long, broken strut. This is illustrated in FIG. 11 which shows a portion 530 of a stent pattern that fractures into a piece 532 and 534 at fracture points 532A and 534A, respectively, resulting in a long broken strut 536 that could cause damage to the vessel. Therefore, It would be desirable to determine precisely where the link will fracture.

Linking struts can be or preprogrammed to selectively fail at particular locations in the link struts in a number of ways. In some embodiments, a recess or hole can be cut at the location on the linking struts where failure it desired. The hole can act as a stress concentrator that hastens the time of failure. In addition to weakening such locations initially, the degradation in such locations will be increased and the fracture and separation adjacent rings will occur sooner. The holes can have openings in the abluminal surface and be cut by laser machining. The time of failure of the linking struts can be adjusted through variation of the diameter and depth of the holes.

The hole can be located at or near the middle of the linking strut where the bending moment is maximal. The diameter of the hole can be, for example, between 50% to 80% of the width of the strut.

Figure 12A:
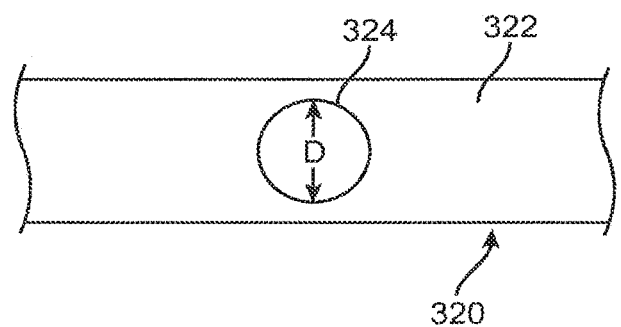
FIG. 12A depicts a view of the abluminal surface of linking strut with a hole.
Figure 12B:
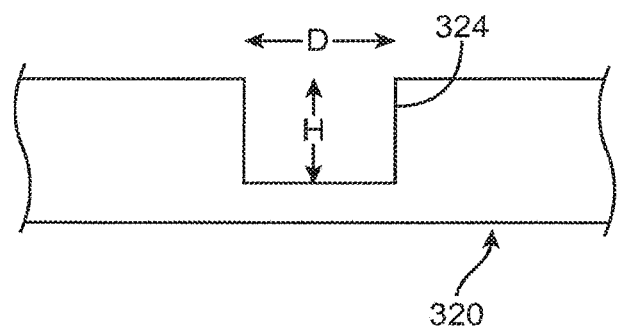
FIG. 12B depicts a cross-sectional side view of the linking strut of FIG. 9A.

The holes in the linking struts can be a through-hole (i.e., all the way through from the abluminal to the luminal surface of the strut) or partially through the thickness of the linking strut (e.g., less than 20%, 40%, 60%, or 80% of the thickness). FIG. 12A depicts an abluminal surface 322 of a linking strut 320 with a hole 324 with a diameter D. FIG. 12B depicts a cross-sectional side view of linking strut 320 showing hole 324 with a depth H. In some embodiments, no other hole or recess is disposed in the struts of the stent other than holes disposed in the links to induce failure, other than holes for radiopaque elements.

In some embodiment, the holes or recesses disclosed herein to induce selective failure are not filled with any material such as polymer, drug, or radiopaque material. Filling such holes or recesses may reduce or prevent the selective failure.

Figure 12C:
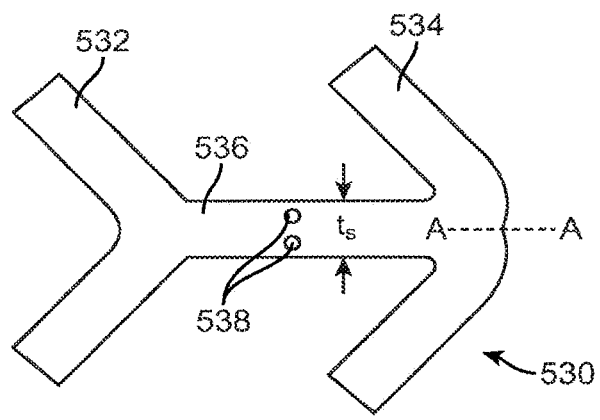
FIG. 12C depicts a portion of a stent pattern with cylindrical strut elements and connected by a link with two holes disposed in the link midway between the cylindrical strut elements.

Additionally, the selective failure of a linking strut can be induced by two or more holes that are closely spaced in a selected region of failure. The holes can be arranged in any number of ways. For example, the holes can be arranged in a line perpendicular to the axis of the stent. This arrangement can provide a more local concentration of the stress along the width of the linking strut. FIG. 12C depicts a portion 530 of a stent pattern with cylindrical ring struts 532 and 534 connected by a link 536. Two holes 538 are disposed midway between the ring struts 532 and 534, although it could be positioned at any location between the rings. The holes are arranged along a line perpendicular to axis A-A, the axis of the stent, although any orientation is possible.

Figure 12D:
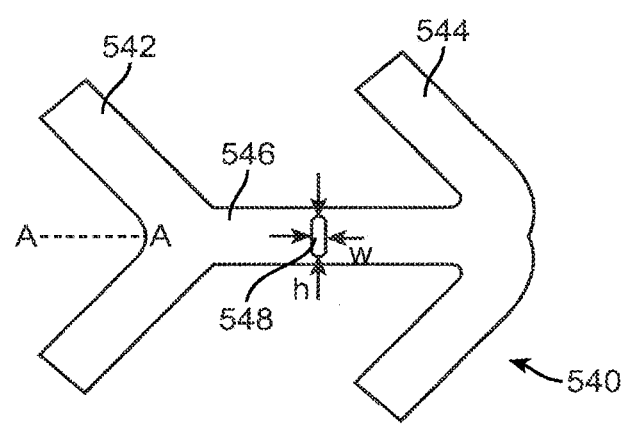
FIG. 12D depicts a portion of a stent pattern with cylindrical strut elements and connected by a link with a slot disposed in the link midway between the cylindrical strut elements.

The recess for inducing selective failure of a linking strut can also be in the form of a notch or slot having an elongated shape with a major axis and a minor axis. A slot refers to a cavity with a narrow opening, such as a groove or slit. The orientation of the slot can be arranged is any number of ways. For instance, the slot can be arranged so its major axis is perpendicular to the axis of the stent. This arrangement can provide a more local concentration of the stress along the width of the link. FIG. 12D depicts a portion 540 of a stent pattern with cylindrical struts 542 and 544 connected by a link 546. A slot 548 is disposed midway between the strut elements 542, although it could be positioned at any location between the rings. The slot is arranged so that its major axis is perpendicular to axis A-A, the axis of the stent, although any orientation is possible. The slot has a height along its major axis, h, and width along minor axis, w. The ratio of h to w can range from 2/1 to 10/1, or where h can vary from 2 to 10 times w. The degree of localization of stress can be controlled by varying h and w. The stress becomes more localized as w decreases and/or h increases. The designs in 12A-12D could be made by laser machining and should also give strut fracture surfaces which are fairly blunt and non-traumatic.

In addition, the selective failure of the linking struts can be induced or facilitated by a region of reduced cross-section along the linking strut. The regions can act as stress concentrators that facilitate fracture and failure. The regions also increase degradation due to the increased surface area. The susceptibility to failure is related to the thickness and length of the reduced cross-section. The thinner and shorter the length, the more concentrated the stress is at the region and the more likely and sooner it will fail. The reduced cross-section regions can be formed by laser cutting.

Figure 13A:
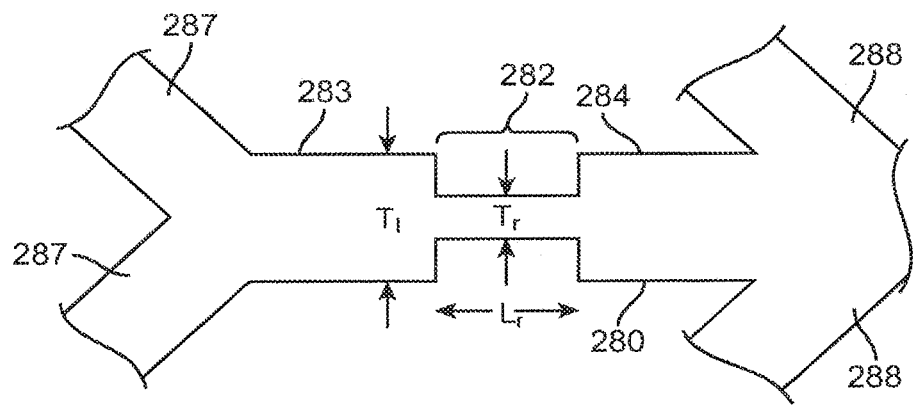
FIG. 13A depicts a linking strut with a reduced cross-section.

FIG. 13A depicts an abluminal surface of a linking strut 280 that is connected to ring struts 287 and 288. Linking strut 280 has a reduced cross-section region 282 between regions 283 and 284. Region 282 has a length Lr and width Tr, the width Tr being less than a width Tl of regions 283 and 284. As Lr and Tr decrease, region 282 becomes more susceptible to fracture.

In some embodiments, the region of reduced cross-section can also be a notch which can easily be cut in the link by laser machining A notch generally, refers to an angular or V-shaped cut, an indentation, or slit in an object, surface, or edge. The notches can be located in the middle of the link, for example. As result, a short piece of link can be left on each ring after failure. This may reduce the likelihood of the cleaved link causing injury to the vessel. The notches also assure that the broken link face will be blunt. This also reduces the chance of the broken link causing injury.

Figure 13B:
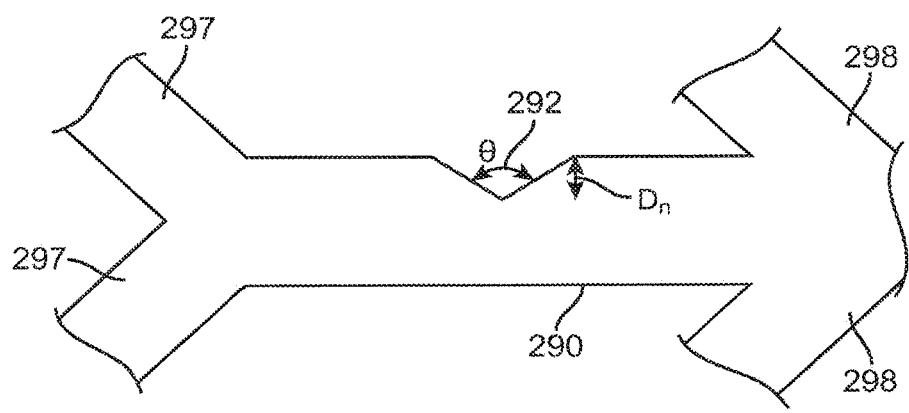
FIG. 13B depicts a linking strut with a notch.
Figure 13C:
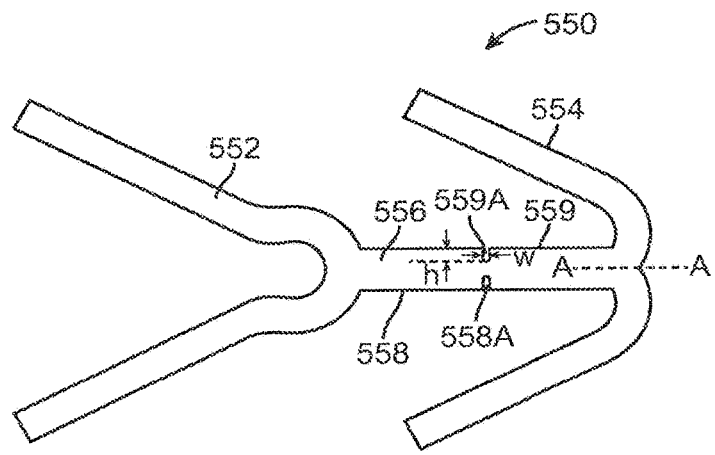
FIG. 13C depicts an abluminal surface of a portion of a stent pattern with notches in opposing side walls of a link connect cylindrical ring strut elements.

A notch can be disposed along a linking strut in the abluminal (outer) surface, luminal surface (inner surface), or sidewalls to induce failure at the position of a notch. There can be one or two symmetric notches. The notches may in one or both of the side wall surfaces. Notches on both sides can be symmetric. FIG. 13B depicts an abluminal surface of a linking strut 290 that is connected to ring struts 297 and 298. Linking strut 290 has a notch 292 with a depth Dn and angle α. As Dn increases and α decreases, region 292 the more concentrated the stress is at the notch and it is believe the more likely and sooner the link strut will fail at the notch. For example, a may be 10-45° and Dn may be 25-75% of the link strut width. FIG. 13C depicts an abluminal surface of a portion 550 of a stent pattern with cylindrical ring struts 552 and 554 connected by a link 556. Link 556 has a notch 558A in a side wall 558 of link 556 and another notch 559A in side wall 559.

The notches extend between the abluminal and luminal surfaces with openings in each surface. The notches are symmetric or directly opposite each other long a line perpendicular to the link axis A-A. This may facilitate fracture in a clean, blunt fashion to avoid trauma to the vessel. However, the links can be offset to allow for different fracture behavior, for example, to delay fracture. The notches 558A and 559A have heights h and widths d. As h increases and w decreases, the more concentrated the stress is at the notch and it is believed the more likely and sooner the link strut will fail at the notch.

Figure 13D:
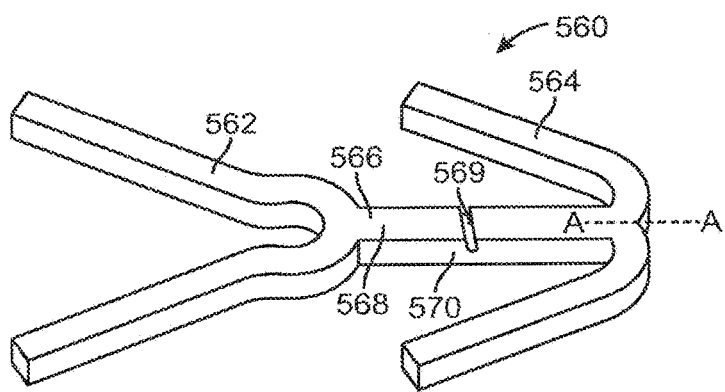
FIG. 13D depicts a portion of a stent pattern with a notches in the abluminal surface of a link connect cylindrical ring strut elements.

Additionally, a link can have a notch on an abluminal side extending from one side wall to the opposite side wall with openings at the sidewall. FIG. 13D depicts a portion 560 of a stent pattern with cylindrical ring struts 562 and 564 connected by a link 566. Link 566 has a notch 569 in an abluminal surface 568 of link 566. The notch extends from side wall 570 to the opposite side wall (not shown) with openings in each side wall surface. The notch extends perpendicular to axis A-A of the link strut.

Figure 13E:
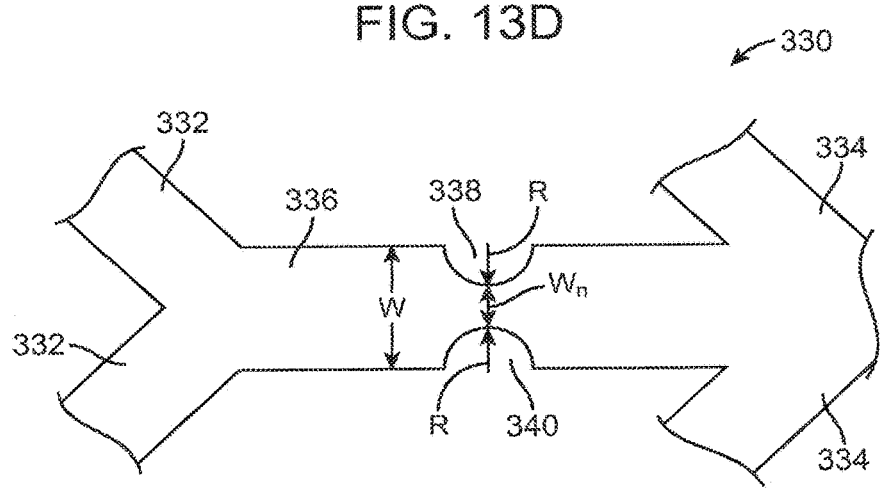
FIG. 13E depicts an abluminal surface of a linking strut with two half circle shaped cavities.

In order facilitate the fracture of the linking struts or specific linking struts, the moment of inertia of a linking strut can be reduced by two opposing half circle-shaped cavities at the edge of the linking strut at or near the middle of its length. FIG. 13E depicts an abluminal surface 336 of a linking strut 330 that is connected to ring struts 332 and 334. Linking strut 330 has two opposing half circle cavities 338 and 340 cut into the side walls of the linking strut. Half circles 338 and 340 have radii R (the radii need not be the same) and the narrowest width of the linking strut between the half circles is Wn. R can be between about 5% and 30% of the width W of the linking strut. R and Wn can be adjusted to obtain desired fracture behavior.

A concern with any strut fracture, even one designed to fracture, is the possibility for vessel wall trauma, dissection, or perforation. Thus, in some embodiments, a link strut having a feature to provides for selective failure, such as a notch, has rounded features adjacent to the notches. In such embodiments, after the link breaks at the notch, the two ends formed by the breakage are then terminated by these rounded features. A rounded feature refers to a structure having curvature or curved surfaces. Rounded features can include structures with shapes that are or are similar to a cylinder, sphere, disc, oblate spheroid, oblate disc, or a cylinder with rounded ends.

In some embodiments, a link strut includes two rounded features positioned along the length of the link strut adjacent and connected to one another. The portion of the link strut extending from the features to the respective ring struts may have a typical straight, elongate strut geometry. The features have a cross-section larger than the straight portion. The features may be connected at a portion of their respective curved surfaces, in a tangential manner, resulting in at least one notch at the connection point. Therefore, the walls that form the notch have curvature. Upon failure at the connection point, the ends of the fractured pieces have rounded or curved surfaces.

By having a rounded feature at the end of the broken link strut, the link strut ends are designed to be as atraumatic to the vessel as possible. If the features, such as discs, represent an undesirable amount of material, the amount of polymer can be reduced by having a hole in the features. In some embodiments, these holes may be filled with radiopaque material, such as platinum-iridium beads, so that the breakable link also serves as a radiopaque marker.

FIG. 14A depicts an abluminal surface of a link 600 having two straight sections 602 and 604, each extending to respective ring struts. The opposite ends of the straight sections include discs 606 and 608 which are connected at their curved surfaces at point 609, forming a notch. As shown, the cylindrical axes of the of the discs is perpendicular to the abluminal surface. FIG. 14B depicts link 600 when the connection point fails after deployment of the stent, the ends 609A and 609B of the two link fragments 600A and 600B are curved or rounded.

FIG. 15A depicts a link 700 having two straight sections 702 and 704, each extending to respective ring struts. The opposite ends of the straight sections include rings 706 and 708 which are connected at their outer curved surfaces at point 709, forming a notch. Each ring 706 and 708 has a hole 705 and 707, respectively. FIG. 15B depicts link strut 700 when the connection point fails after deployment of the stent, the ends 709A and 709B of the two link fragments 700A and 700B are curved or rounded.

Alternatively or additionally, oblate disc features may be used to reduce the amount of material in a feature. FIG. 16A depicts a link strut 800 having two straight sections 802 and 804, each extending to respective ring struts. The opposite ends of the straight sections include oblate discs 806 and 808 which are connected at their outer curved surfaces at point 809, forming a notch. The oblate discs 806 and 808 have major axes h and minor axes w. The oblate discs are arranged so that minor axes are parallel with the link axis A-A. In an alternative embodiment, the oblate discs can be arrange so that their major axes are parallel to the link axis. FIG. 16B depicts link 800 when the connection point fails after deployment of the stent, the ends 809A and 809B of the two link fragments 800A and 800B are curved or rounded.

In further embodiments, the rounded features can include curved segments or arcs that are connected to ends of straight sections. The width of the curved segments may be the same or similar to the width of the straight segments of the link strut. Alternatively, the width of the curved segments may be greater than or less than the width of the straight segments. The straight sections in combination with the curved segment may have the appearance of an anchor-shape.

FIG. 17A depicts a link 900 having two straight sections 902 and 904, each extending to respective ring struts. The opposite ends of the straight sections are connected to curved segments 906 and 908. Curved segments 906 and 908 are connected to the straight sections at their concave surfaces half-way along the length of the curved segments, but could be connected at other locations along curved segments. The curved segments are connected at their convex curved surfaces at point 909, forming two symmetric notches. The width of the curved segments, wc, is shown to be the same as the width ws of the straight segments. As mentioned above, wc can be greater than or less than ws.

FIG. 17B depicts link 900 when the connection point fails after deployment of the stent, the ends 909A and 909B of the two link fragments 900A and 900B are curved or rounded.

The stent of the can be made from variety of biodegradable polymers including, but not limited to, poly(L-lactide) (PLLA), polymandelide (PM), poly(DL-lactide) (PDLLA), polyglycolide (PGA), polycaprolactone (PCL), poly(trimethylene carbonate) (PTMC), polydioxanone (PDO), poly (4-hydroxy butyrate) (PHB), and poly(butylene succinate) (PBS). The stent can also be made from random and block copolymers of the above polymers, in particular, poly(L-lactide-co-glycolide) (PLGA) and poly(L-Lactide-co-caprolactone) PLGA-PCL. The stent can be made from PLGA including any molar ratio of L-lactide (LLA) to glycolide (GA). In particular, the stent can be made from PLGA with a molar ratio of (LA:GA) including 85:15 (or a range of 82:18 to 88:12), 95:5 (or a range of 93:7 to 97:3), or commercially available PLGA products identified as having these molar ratios. High strength, semicrystalline polymers with a Tg above body temperature include PLLA, PGA, and PLGA. High fracture toughness polymers include PCL, PTMC, PDO, PHB, and PBS.

"Radial strength" of a stent is defined as the pressure at which a stent experiences irrecoverable deformation.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that result from the applied force. For example, a material has both a tensile and a compressive modulus.

The underlying structure or substrate of an implantable medical device, such as a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent for treating a diseased section of a blood vessel, comprising:
    a bioabsorbable polymeric scaffolding composed of a pattern of struts, the pattern comprising a first cylindrical ring of struts and a second cylindrical ring of struts,
    wherein the first ring and the second ring are connected by a set of breakable linking struts,
    wherein each breakable linking strut has two discs disposed between the rings, each of the discs having an unfilled hole,
    wherein the discs are in contact and connected at their curved surfaces which forms a notch at the connection point, wherein after deployment of the stent in a vessel of a patient each link breaks at the connection point prior to struts in the cylindrical rings.

2. The stent of claim 1, wherein the connected discs of at least one breakable linking strut comprising the holes through each disc form a donut-like structure.

3. The stent of claim 1, wherein the connected discs of at least one breakable linking strut are circular.

4. The stent of claim 1, wherein the connected discs of at least one breakable linking strut are oblate discs connected at their surfaces along their major axes.

5. The stent of claim 1, wherein the cylindrical axes of the discs are perpendicular to the abluminal surface.

* * * * *